United States Patent [19]
Bauman

[11] 3,961,075
[45] June 1, 1976

[54] ETHER-LINKED QUATERNARY AMMONIUM COMPOSITIONS

[75] Inventor: Robert Andrew Bauman, New Brunswick, N.J.

[73] Assignee: Colgate-Palmolive Company, New York, N.Y.

[22] Filed: May 9, 1975

[21] Appl. No.: 576,084

Related U.S. Application Data

[60] Division of Ser. No. 445,714, Feb. 25, 1974, Pat. No. 3,898,284, which is a continuation-in-part of Ser. No. 400,097, Sept. 24, 1973, which is a continuation of Ser. No. 39,536, May 21, 1970, abandoned.

[52] U.S. Cl. ................................. 424/54; 424/329
[51] Int. Cl.$^2$ .................................. A61K 7/22
[58] Field of Search ............................ 424/329, 54

[56] References Cited
UNITED STATES PATENTS

3,565,942    2/1971    Krimmel ............................ 260/468

Primary Examiner—Jerome D. Goldberg
Attorney, Agent, or Firm—Robert L. Stone; Murray M. Grill; Herbert S. Sylvester

[57] ABSTRACT

Novel quaternary ammonium compounds containing one large aliphatic group, and an adamantyl group linked to the quaternary nitrogen by an ether group.

6 Claims, No Drawings

ETHER-LINKED QUATERNARY AMMONIUM COMPOSITIONS

This is a division of application Ser. No. 445.714 filed Feb. 25, 1974 now U.S. Pat. No. 3,898,284 issued Aug. 5, 1973 which is a continuation in part of copending application Ser. No. 400,097, filed Sept. 24, 1973, which is a continuation of patent application 39,536 filed May 21, 1970 now abandoned.

The present invention relates to novel quaternary ammonium compounds represented by the general formula:

wherein R is 1-adamantyl ($C_{10}H_{15}$), $R^1$ is an aliphatic chain containing 10-18 carbon atoms, n is an integer from 2 to 3 and X is a compatible anion such as the halides ($Cl^-, Br^-, I^-$), sulfates (i.e., methyl sulfate), nitrates, aryl sulfonates, etc. These quaternary compounds possess superior antimicrobial, anti-caries, and anticalculus activity.

The adamantyl radical is derived from tricyclo[$3.3.1.1^{3,7}$]decane showing four fused chair cyclohexane rings as follows:

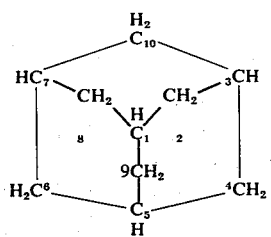

Typical examples of the quaternary ammonium compounds which may be used in this invention are:

2-($1^1$-adamantyloxy)ethyldimethyldodecyl ammonium bromide,
2-($1^1$-adamantyloxy)ethyldimethyltetradecyl ammonium bromide,
2-($1^1$-adamantyloxy)ethyldimethyldecyl ammonium chloride,
2-($1^1$-adamantyloxy)ethyldimethylhexadecyl ammonium chloride,
2-($1^1$-adamantyloxy)ethyldimethyloctadecyl ammonium chloride,
3-($1^1$-adamantyloxy)propyldimethyldodecyl ammonium bromide.

Other halides such as the iodides and analogous compounds such as the sulfates, nitrates, aryl sulfonates, etc. may also be employed herein as effective anti-bactericides.

It has been observed that the compounds generally described by the foregoing formula are particularly effective against a wide range of organisms including the gram positive organisms such as *Staphylococcus aureus; Streptococcus mitis, sanguis* and *mutans; Bacillus subtilis; Corynbacterium acnes;* and especially effective against fungi, such as *Candida albicans, Trichophyton mentogrophytes* and *Aspergillus niger,* and against *Escherichia coli* which is a gram negative bacteria. Compounds wherein $R^1$ is a benzyl radical in lieu of instant higher alkyl radical would be devoid of antibacterial activity.

The anti-microbial nature of the instant novel compounds was shown by a standard test tube serial dilution test in which an appropriate number of test tubes of broth containing decreasing concentrations of the test agent was innoculated with the test organism. After a suitable period of incubation, the tubes were examined for the presence or absence of growth. The activity of the test agent was the lowest concentration which inhibited the growth of the organism and is expressed as the minimal inhibitory concentration in ug/ml.

TABLE I:

Minimum Inhibitory Concentration ($\mu$g/ml)

$[ROCH_2CH_2N(CH_3)_2R^1]^+Br^-$

|  | $R^1=C_{14}H_{29}$ | $C_{12}H_{25}$ |
|---|---|---|
| S. *aureus* | 0.78 | 0.39 |
| Str. *mitis* | 0.39 | 0.19 |
| C. *albicans* | 1.56 | 1.56 |
| P. *ovale* | >50 | >50 |
| T. *mentagrophytes* | 6.25 | 3.12 |
| Ps. *aeruginosa* | >25 | >25 |
| A. *niger* | 50 | 50 |
| E. *coli* | 12.5 | 12.5 |

These dilution tests evidence the effectiveness of compounds of the invention against bacteria and fungi.

When used against bacteria or fungi, compounds of the instant invention may be applied directly to the surface to be protected or may be dissolved in a pharmaceutical carrier. Typically, an effective amount, e.g., 0.1 to about 10% by weight of the compound, is included in an inert carrier and a dispersing or surface-active agent. Alternatively, an effective amount, e.g. 0.1 to about 10% by weight may be incorporated into a solid carrier which may be inert, such as talc, clay, diatomaceous earth, flour, etc.

When compounds of the instant invention are intended for use in compositions which reduce formation of caries and inhibit formation of oral calculus, they are typically incorporated in oral preparation in effective amounts up to about 5% by weight, preferably .025–1% and most preferably 0.5–0.5% by weight of the oral preparation. Typically, the oral preparation is a dentifrice, such as a dental cream tablet or powder, containing as a vehicle about 20–95% by weight of a water-insoluble polishing material, preferably including water-insoluble phosphate such as dicalcium phosphate, tricalcium phosphate, trimagnesium phosphate. The dentrifrice may also include water; binders such as glycerine, sorbitol, propylene glycol and polyethylene glycol 400; detergents; gelling agents such as Irish moss and sodium carboxy methyl cellulose; additional antibacterial agents; coloring or whitening agents; preservatives; silicones; chlorophyll compounds; additional ammoniated materials; flavoring or sweetening materials; and compounds which provide fluorine-containing ion such as sodium fluoride, stannous fluoride and sodium monofluorophosphate.

The oral preparation may also be a liquid such as mouth rinse which typically contains 20–99% by weight of an aqueous lower aliphatic alcohol, preferably having about 1–30% by weight alcohol, such as ethanol, n-propyl, or isopropyl alcohol.

Such oral preparations are typically applied by brushing the teeth or rinsing the oral cavity for 30–90 seconds at least once daily. Typical oral preparations of the invention which can be applied in this manner are set forth below.

EXAMPLE I

Dental Cream

| | % |
|---|---|
| 2(1'-adamantyloxy)ethyldodecyldimethyl ammonium bromide | 0.50 |
| Nonionic detergent* | 1.00 |
| Glycerine | 22.00 |
| Sodium pyrophosphate | 0.25 |
| Carboxymethyl cellulose | 0.85 |
| Sodium saccharin | 0.20 |
| Sodium benzoate | 0.50 |
| Calcium carbonate (precipitated) | 5.00 |
| Dicalcium phosphate dihydrate | 46.75 |
| Flavor | 0.80 |
| Water | 22.15 |

*Tween 80 - Polyoxyethylene (20 moles ethylene oxide) sorbitan monooleate.

EXAMPLE 2

Mouthwash

| | % |
|---|---|
| 2-(1'-adamantyloxy)ethyltetradecyldimethyl ammonium bromide | 0.05 |
| Nonionic detergent (Pluronic F-68)* | 1.00 |
| Ethyl alcohol (containing flavor) | 15.00 |
| Glycerine | 10.00 |
| Saccharin | 0.02 |
| Water | 73.73 |

*Block polymer of 80% polyoxyethylene and 20% polyoxypropylene.

The quaternary ammonium ethers of instant invention can be prepared by a two-step method of reacting a 1-haloadamantane with dimethyl aminoethanol to form a tertiary amino ether and subsequently quaternising with an alkyl halide or ester of sulfuric or of arenesulfonic acid (i.e. methyl toluene sulfonate) as illustrated by the following equations wherein R and R¹ have the aforedefined meanings.

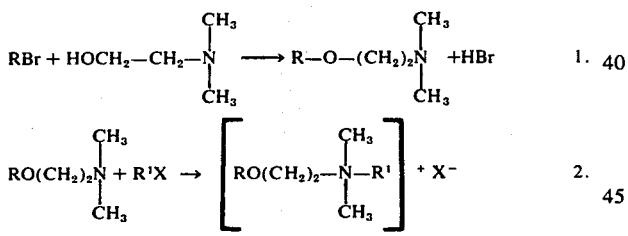

The following examples illustrate the manner in which compounds of this invention are prepared.

EXAMPLE 3

Preparation of 2(1'-adamantyloxy)ethyldimethyltetradecylammonium bromide: A mixture of 600 g. (2.8 moles) 1-bromoadamantane and 1250 g. (14 moles) 2-dimethylaminoethanol was stirred and refluxed for 48 hours. At this time the reaction mixture was divided in two and each portion worked up as follows: Half the mixture was poured into 2 l. water and extracted three times with 500 ml. portions of ether. The ether solution was extracted three times with portions of a solution of 300 ml. concentrated hydrochloric acid in 2.2 l. water. This aqueous acidic extract was then treated with a solution of 360 g. sodium hydroxide in 1 l. water. The liberated product was then extracted from the suspension with four 500-ml. portions of ether. The ether extract was washed twice with 200-ml. portions of water and once with saturated sodium sulfate solution. The ether extract was dried over sodium sulfate and combined with the similar extract obtained from the other half of the original reaction mixture. After removal of the solvent the product was distilled in vacuum through an 18" Vigreux column. Distillate collected at 118°–120° (1.6T) was homogenous and free of starting materials by GC (Apiezon L column). Analysis: Neutral equivalent: 223.4, calcd; 226.9, found. A solution of 580 g. (2.6 moles) of 1-(2¹-dimethylaminoethoxy) adamantane and 720 g. (2.6 moles) 1-bromotetradecane in 5 l. acetone was refluxed for 40 hours. The hot solution was treated with Norite and allowed to crystallize. After a second recrystallization from acetone and drying in vacuum at room temperature, 1036 g. material was obtained (80% of theory); m.p. 133°–135°.

Analysis: Calcd. for $C_{28}H_{54}BrOn$: C, 67.17; H, 10.87; Br, 15.96.
Found: C, 67.21; H, 10.90; Br, 15.96.

EXAMPLE 4

The dodecyl homolog was prepared by the procedure of Example 3, yielding hygroscopic crystals having a melting point when dry of 128°–130°C and the following analysis:

| | Found | Calculated |
|---|---|---|
| Bromine | 16.91 | 16.91 |

Although this invention has been described with reference to specific examples, it will be apparent to one skilled in the art that various modifications may be made thereto which fall within its scope.

What is claimed is:

1. A pharmaceutical composition comprising about 0.1–10% by weight of a chemical compound having the structural formula: $RO(CH_2)_nN(CH_3)_2R^1 {}^+ X^-$ wherein R is 1-adamantyl, $R^1$ is a long chain alkyl group of 10 to 18 carbon atoms, n is an integer from 1 to 3, and X is a compatible anion selected from the group consisting of chloride, bromide, iodide, methyl sulfate, nitrate and arylsulfonates.

2. A pharmaceutical carrier as set forth in claim 1, wherein X is a halide.

3. An oral preparation comprising an effective amount to reduce caries formation and inhibit calculus formation up to about 5% by weight of a chemical compound having the structural formula: $RO(CH_2)_nN(CH_3)_2R^1 {}^+ X^-$ wherein R is 1-adamantyl, $R^1$ is a long chain alkyl group of 10 to 18 carbon atoms, n is an integer from 1 to 3, and X is a compatible anion admixed with an oral vehicle selected from the group consisting of chloride, bromide, iodide, methyl sulfate, nitrate and arylsulfonates.

4. An oral preparation as set forth in claim 3 wherein said compound is 2-(1¹-adamantyloxy)ethyldimethyldodecyl ammonium bromide.

5. An oral preparation as set forth in claim 3 wherein said compound is 2-(1¹-adamantyloxy)ethyldimethyltetradecyl ammonium brodime.

6. An oral preparation as set forth in claim 3 wherein said compound is present in amount of about 0.025-1% by weight.

* * * * *